(12) United States Patent
Geiger et al.

(10) Patent No.: US 9,681,729 B2
(45) Date of Patent: Jun. 20, 2017

(54) TUBE HEAD FOR PROVISION AND APPLICATION OF A LIQUID AND TUBE WITH SUCH A TUBE HEAD

(71) Applicant: HOFFMANN NEOPAC AG, Thun (CH)

(72) Inventors: Andreas Geiger, Heimberg (CH); Jan Mathys, Oberdiessbach (CH)

(73) Assignee: HOFFMANN NEOPAC AG, Thun (CH)

( * ) Notice: Subject to any disclaimer, the term of this patent is extended or adjusted under 35 U.S.C. 154(b) by 0 days.

(21) Appl. No.: 14/894,751

(22) PCT Filed: Jun. 28, 2013

(86) PCT No.: PCT/CH2013/000117
§ 371 (c)(1),
(2) Date: Nov. 30, 2015

(87) PCT Pub. No.: WO2014/205587
PCT Pub. Date: Dec. 31, 2014

(65) Prior Publication Data
US 2016/0106196 A1    Apr. 21, 2016

(51) Int. Cl.
*B65D 47/40* (2006.01)
*A45D 34/04* (2006.01)
(Continued)

(52) U.S. Cl.
CPC .......... *A45D 34/042* (2013.01); *A45D 34/04* (2013.01); *A61F 9/0008* (2013.01); *B65D 47/18* (2013.01); *B65D 47/42* (2013.01)

(58) Field of Classification Search
CPC ....... B65D 23/06; B65D 23/065; B65D 47/40
(Continued)

(56) References Cited

U.S. PATENT DOCUMENTS 2,982,987 A * 5/1961 Knapp ................... B43M 11/06
                                                         15/236.08
4,192,360 A * 3/1980 Rodriquez ............ A61J 7/0053
                                                         141/24
(Continued)

FOREIGN PATENT DOCUMENTS

EP        093493 A1    11/1983
EP       0354823 A1     2/1990
EP       0612488 A1     8/1994

OTHER PUBLICATIONS

International Search Report, Application No. PCT/CH2013/000117, dated Apr. 7, 2014.

*Primary Examiner* — David Walczak
*Assistant Examiner* — Joshua Wiljanen
(74) *Attorney, Agent, or Firm* — Marshall, Gerstein & Borun LLP (57) ABSTRACT

The present invention relates to a tube head (1) for provision and application of a liquid, the tube head (1) comprising a spout (3) with an opening (5) for dispensing the liquid in the form of drops, wherein an applicator (4) is provided, the applicator (4) being attached to the spout (3) and extending in the longitudinal direction of the spout (3), wherein the applicator (4) comprises receiving means (16) for receiving the liquid dispensed by the spout (3) and wherein a gap (17) is provided between the receiving means (16) and the opening (5) of the spout (3) in the longitudinal direction. The invention furthermore relates to a tube (30) with such a tube head (1). Gap sizes may differ for different tube heads and tubes, respectively.

21 Claims, 8 Drawing Sheets

(51) Int. Cl.
*A61F 9/00* (2006.01)
*B65D 47/18* (2006.01)
*B65D 47/42* (2006.01)

(58) Field of Classification Search
USPC .......... 401/15, 130, 261, 263; 222/207, 420
See application file for complete search history.

(56) References Cited

U.S. PATENT DOCUMENTS

| | | | |
|---|---|---|---|
| 5,333,967 A * | 8/1994 | Foley | B26B 27/00 |
| | | | 156/750 |
| 6,197,008 B1 | 3/2001 | Hagele | |
| 8,517,219 B1 * | 8/2013 | Prince | G01F 11/028 |
| | | | 141/22 |
| 8,662,780 B2 * | 3/2014 | Fontana | A45D 34/04 |
| | | | 401/132 |

\* cited by examiner

TUBE HEAD FOR PROVISION AND APPLICATION OF A LIQUID AND TUBE WITH SUCH A TUBE HEAD

CROSS-REFERENCE TO RELATED APPLICATIONS

This is the United States National Phase of International Patent Application No. PCT/CH2013/000117, filed Jun. 28, 2013, the entire contents of which are hereby incorporated by reference.

TECHNICAL FIELD

The invention relates to a tube head for provision and application of a liquid and to a tube with such a tube head. Typical application areas are among others in pharmaceutics and cosmetics. The term "tube" shall also comprise bottles and other containers that have to be squeezed to dispense their contents.

BACKGROUND

When dispensing liquid in form of drops, e.g., as eye drops, from a tube the size of the drops depends on properties of the liquid such as viscosity and surface tension and on properties of the break-away area of the spout of the tube, i.e., the properties of the area at which the drop breaks away from the liquid flowing to the spout opening. Such properties are in particular the size of the break-away area and its surface tension compared with the surface tension of the liquid. Hence, with the properties of the liquid set the drop size can only be influenced through variations of the break-away area.

Furthermore, typically a drop has to fall to be applied (as, e.g., with drops applied to the eye or skin) or to be further used as with indirect applications.

It is known in the state of the art to provide for different drop sizes by either enlarging or reducing the break-away area at the dispensing end of the spout. For example, the outer diameter of the break-away area is often enlarged for tubes and (also non-squeezable) bottles for dispensing eye drops. However, varying drop sizes by providing break-away areas of different sizes is rather cost-intensive.

If the dispensed drops shall be indirectly used, they are typically dropped onto a spatula or a brush. The spatula or brush, respectively, is then used to apply the liquid. However, the user needs two hands, one hand for squeezing the tube to dispense the liquid, the other hand for holding the spatula or brush.

DISCLOSURE OF THE INVENTION

It is an object of the invention to provide a tube head and a tube by which indirect application of liquid, in particular liquid drops, is easier for the user. It is a further object of the invention to provide a tube head and a tube that allow for simpler, less cost-intensive variation of drop size. It is a further object of the invention to provide a tube and a tube head by which the doses of the liquid, in particular the amount of drops, to be applied can be better controlled.

In order to implement these and still further objects of the invention, which will become more readily apparent as the description proceeds, a tube head for provision and application of a liquid is provided, the tube head comprising a spout with an opening for dispensing the liquid in the form of drops and an applicator that is attached to the spout, extending in the longitudinal direction of the spout. The applicator comprises means for receiving the liquid, in particular the drops, dispensed from the spout. A gap is provided between the receiving means and the opening of the spout in the longitudinal direction.

The applicator is preferably detachable from the spout, such that it may be replaced by an applicator with a different gap size. The gap size between receiving means and spout opening and thus between receiving means and break-away point/break-away area of the spout determines the size of the drops received by the receiving means. Hence, by means of the gap size the amount of liquid received by the receiving means can be regulated. Furthermore, for liquids with different properties such as different viscosity different applicators with appropriately chosen gap sizes can be employed.

The receiving means of the applicator preferably comprise a surface for receiving the liquid dispensed in the form of drops from the spout, the surface preferably being flat (forming in particular a spatula) such that the received liquid can easily flow in the longitudinal direction to the end of the surface that is distal to the opening of the spout. With such a surface the received liquid can be easily applied, for example to human skin. In addition or alternatively the receiving means may comprise a sponge or a brush for application of the received liquid. The sponge and the brush, respective, may be removable, such that the user can only attach them if needed.

A set of tube heads with at least two tube heads may be provided, wherein for different tube heads the size of the gap of the applicator is different. In such manner a set of tube heads is provided, wherein with different tube heads liquid can be dispensed in different drop sizes.

The present invention further relates to a tube with a tube head according to the invention and a tube body, wherein the tube head is connected to the tube body, the tube body containing the liquid to be dispensed. The tube head preferably comprises an insert with a throttling part, the throttling part having a throttling passage, for example a notch, through which the liquid must flow to reach the opening of the spout. Such an insert is, for example, disclosed in International Patent Application WO-A1 2013/075256 of the applicant.

Squeezing the tube body causes the liquid to flow—in particular through the throttling passage of the insert—through the spout and to detach itself from the spout's opening in form of a drop. However, before the drop becomes fully detached/fully breaks away it bridges the gap and is caught/received by the receiving means of the applicator, wetting the receiving means. Hence, the drop is drawn onto the receiving means, preferentially without dragging along a further drop (unless, of course, in case of further squeezing of the tube body). The receiving means may in particular be in the form of a spatula as outlined above, with the drop(s) flowing to its distal end. The resulting drop size is advantageously independent of the pressure exerted onto the tube body during squeezing.

Thus, more exact dosing of the liquid to be applied can be achieved as the number of drops crossing the gap can be counted. Hence, the amount of liquid to be applied can be easily controlled.

Advantageously, a user only needs one hand to dispense liquid from the tube of the invention as the liquid is dispensed directly onto the applicator, thereby wetting the applicator (i.e., its receiving means) with the liquid for further application. I.e., as the applicator is attached to the tube the user does not need to separately hold it and can freely use his second hand for other purposes, i.e. holding a tissue to absorb excess liquid. This one-hand-use is also of advantage in case the liquid shall be applied to a hand, e.g., fingernails. With the wetted applicator/receiving means the liquid may be directly distributed onto its destination, e.g., onto skin or a fingernail.

Gap sizes may differ for different tube heads and tubes, respectively. As with the tube heads, a set of tubes may be provided that comprises at least two tubes according to the invention, wherein for different tubes the size of the gap of the applicator of the tube head is different. In such manner a set of tubes can be provided, wherein with different tubes liquid can be dispensed in different drop sizes.

The liquid dispensed may in particular be a liquid pharmaceutical or cosmetic product such as a serum that shall be applied to the skin for rejuvenation/regeneration.

BRIEF DESCRIPTION OF THE DRAWINGS

Further advantageous features and applications of the invention can be found in the dependent claims as well as in the following description of the drawings illustrating the invention. In the drawings like reference signs designate the same or similar parts throughout the several figures of which:

Dimensions in the drawings are mentioned by way of example only. The unit shall be millimeters.

MODE(S) FOR CARRYING OUT THE INVENTION

Figure 1:
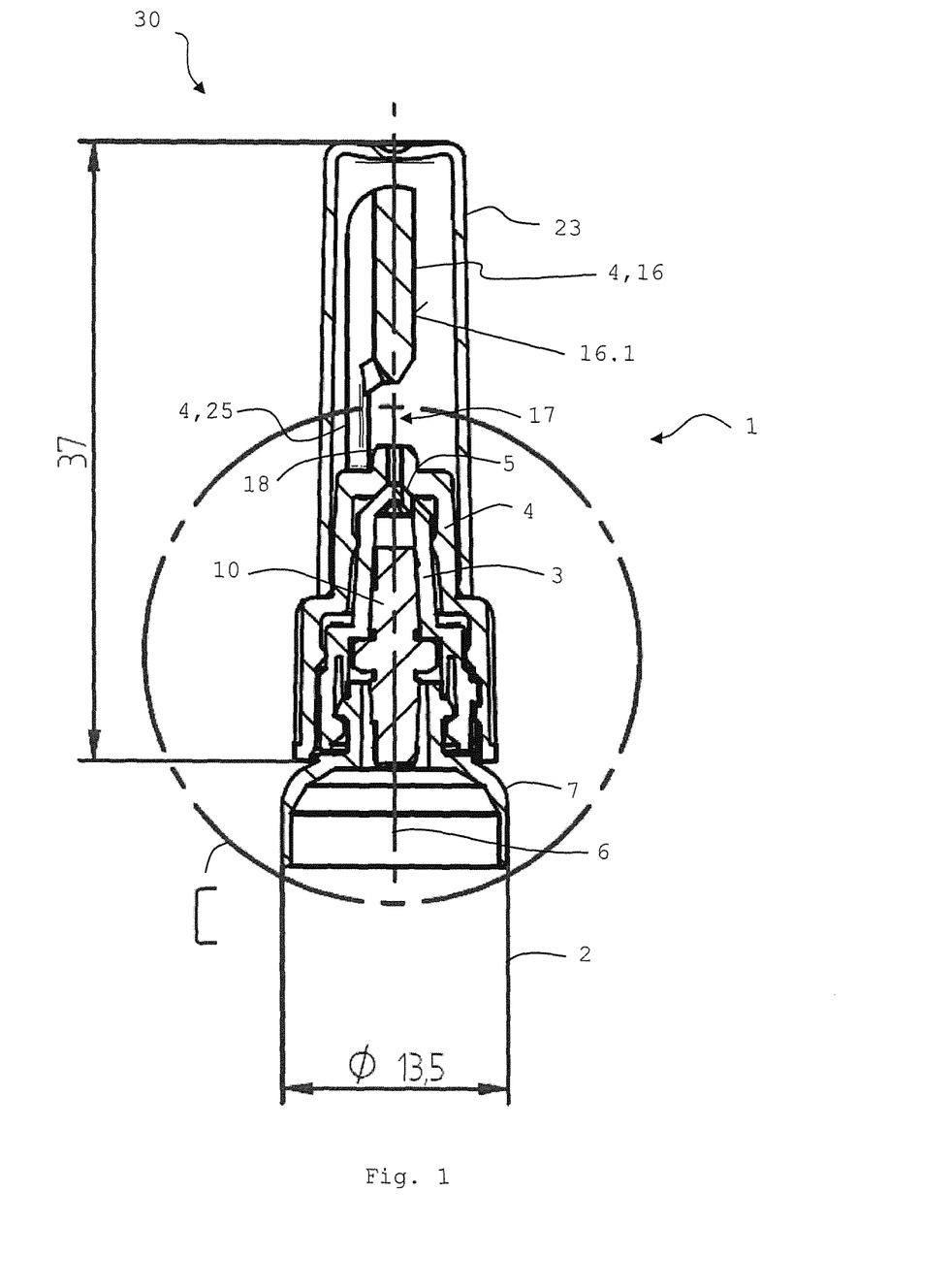
FIG. 1 shows a cross-sectional view of a tube according to the invention.
Figure 2:
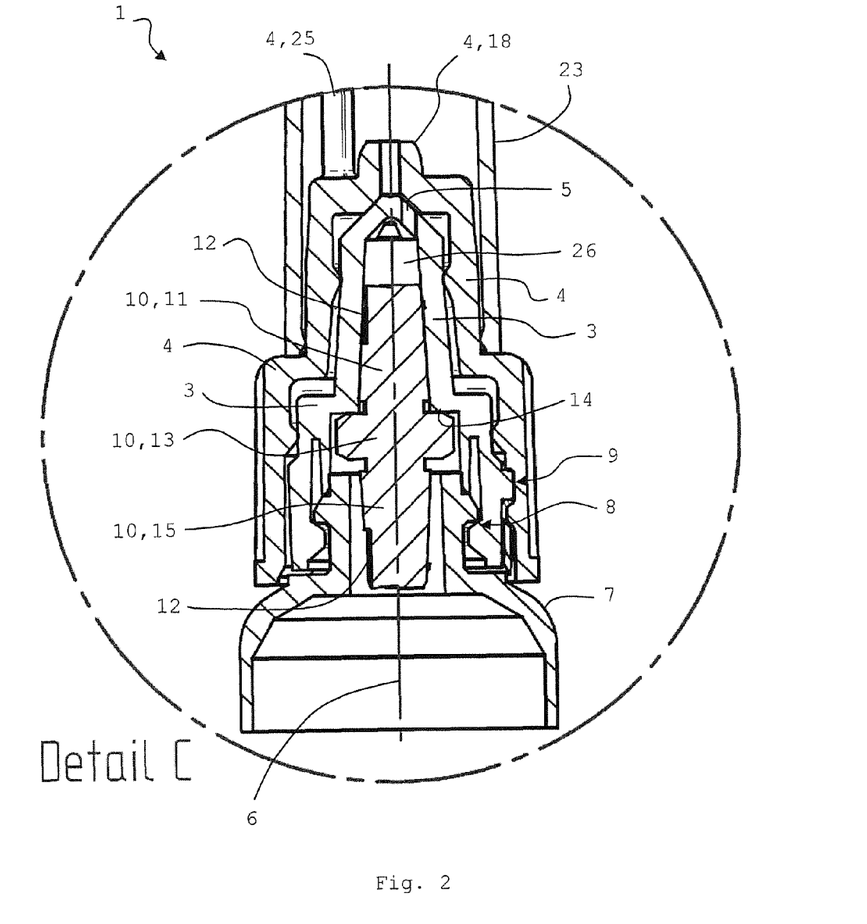
FIG. 2 shows a cross-sectional view of a detail of the tube shown in FIG. 1.

FIGS. 1 and 2 shows a tube 30 with a tube head 1 according to the invention that is connected to a tube body 2, the tube body 2 containing liquid (not shown) to be dispensed. For simplicity only the top of the tube body 2 is shown.

Figure 3:
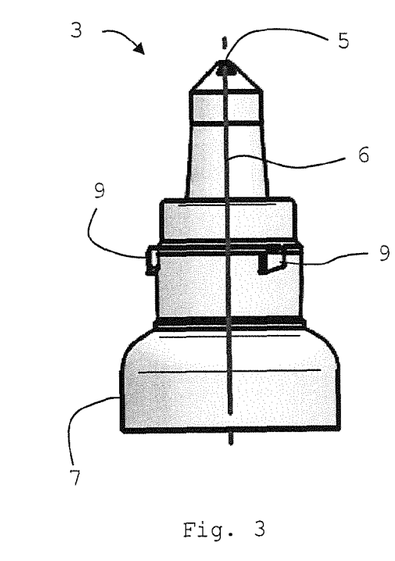
FIG. 3 shows a front view of a spout of a tube head according to the invention.
Figure 4:
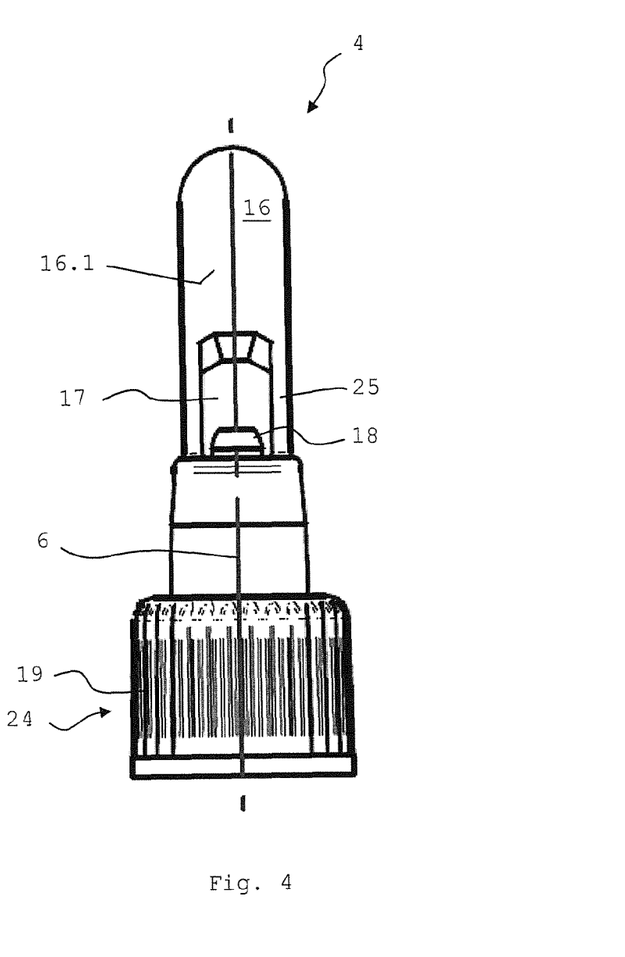
FIG. 4 shows a front view of an applicator of a tube head of the invention.
Figure 5:
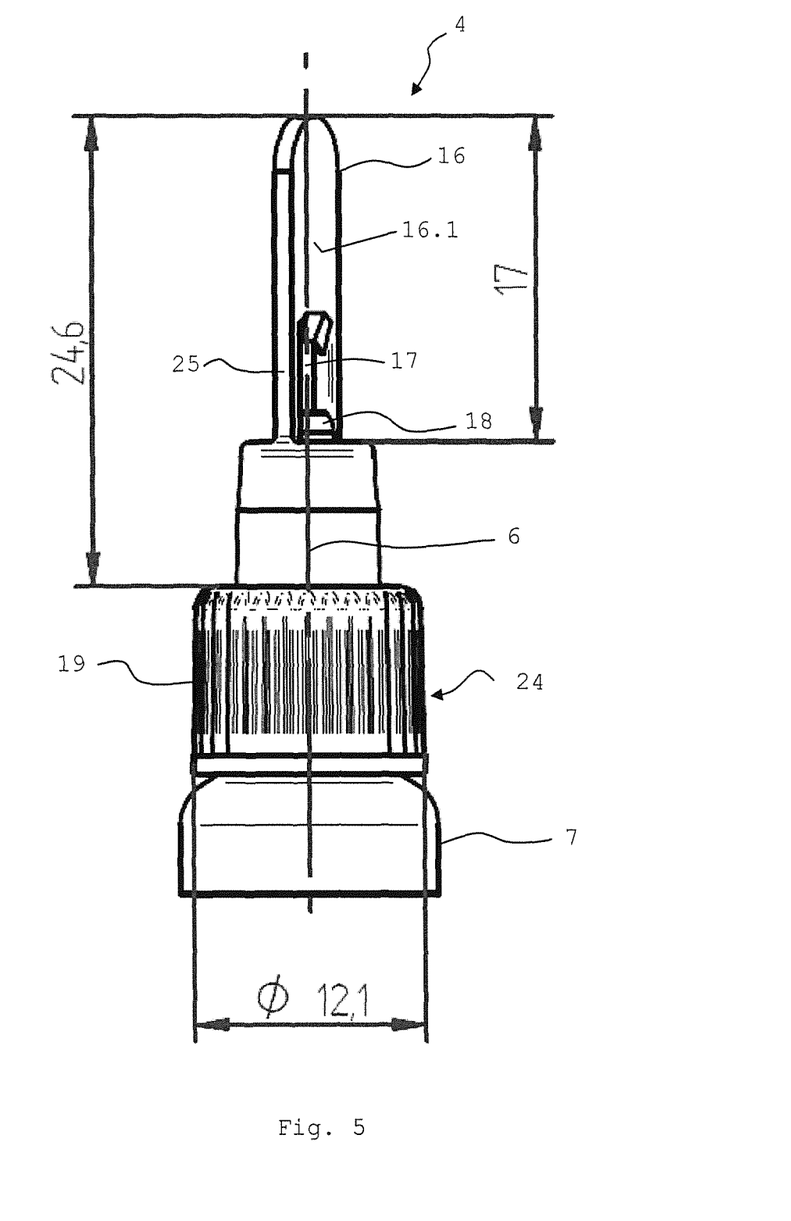
FIG. 5 shows a tube head according to the invention.

The tube head 1 comprises a spout 3 and an applicator 4 that is removably attached to the spout 3. Front views of spout 3 and applicator 4 are shown in FIGS. 3 and 4. A front view of the tube head 1 according to the invention with the applicator 4 placed on the spout 3 is shown in FIG. 5.

The spout 3 has an opening 5 though which liquid can be dispensed in form of drops. The spout 3 narrows in the longitudinal direction 6 toward its opening 5. At the end distal from the opening 5 the spout 3 may be provided with a shoulder 7, the shoulder 7 being attached to the rest of the spout 3, e.g., by snap-on means 8. The spout 3 is then connected to the tube body 2 by means of the shoulder 7. Alternatively, the shoulder 7 may form part of the tube body 2 or even a separate piece, with the spout 3 being attached to the shoulder 7, e.g., by snap-on means 8.

For connecting the applicator 4 detachably to the spout 3 locking means 9 are provided on the inner surface of the applicator 4 and/or the outer surface of the spout 3, the respective surfaces facing each other (see FIGS. 2 and 3). The locking means 9 may, for example, be formed as projection on the one surface engaging with an indentation on the other, opposite surface.

Inside the spout 3 preferentially an insert 10 with a throttling part 11 is arranged. The outer diameter of the throttling part 11 preferably matches the inner diameter of the spout 3 at its destined position such that there is a tight fit between throttling part 11 of the insert 10 and spout 3 at the destined position. The throttling part 11 has at least one throttling passage 12 through which liquid from the tube body 2 has to pass to reach the opening 5 of the spout 3. Preferably there is some space 26 provided between the opening 5 and the end of the insert 10 that is proximal to the opening 5 for liquid to gather.

During manufacturing the insert 10 is pushed into the spout 3. To simplify accurate positioning of the insert 10 and thus its throttling part 11 inside the spout 3, the insert 10 has a broader middle part 13 that is designed to abut against an inner annular rim 14 of the spout 3, the inner annular rim 14 having an inner diameter that is smaller than the diameter of the middle part 13 of the insert 10. Furthermore, a handle 15 may be provided at the side of the middle part 13 that is opposite to the throttling part 11. The diameter of the handle 15 may be smaller than the diameter of the middle part 13. The throttling passage 12 may extend through the entire insert 10. It may be curved and/or straight.

The applicator 4 (see FIGS. 1, 4 and 5) comprises receiving means 16 for receiving a liquid drop dispensed from the opening 5 of the spout 3. Placed on the spout 3 a gap 17 is formed between the opening 5 of the spout 3 and the end of the receiving means 16 that is proximal to the opening 5. The applicator 4 may comprise an orifice 18 that is placed on top of the opening 5 of the spout 3. The orifice 18 helps guiding the liquid drop onto the receiving means 16. On its sides the gap 17 is preferably limited by racks 25.

The applicator 4 may be provided with a grabbing part 24 for easier handling and attaching to the spout 3. The grabbing part 24 preferably comprises the applicator parts of the locking means 9 on its inside. The grabbing part 24 is located such that the applicator parts of the locking means 9 engage with the parts of the locking means 9 that are arranged on the outside of the spout 3. The outer surface of the grabbing part 24 is preferably provided with ripples 19 for easier handling. The ripples 19 are in particular annularly distributed on the outer surface of the grabbing part 24.

The receiving means 16 preferably have a flat surface 16.1, in particular a spatula, on which drops dispensed from the opening 5 of the spout 3 can gather for further application by means of the flat surface 16.1/the spatula.

Figure 6:
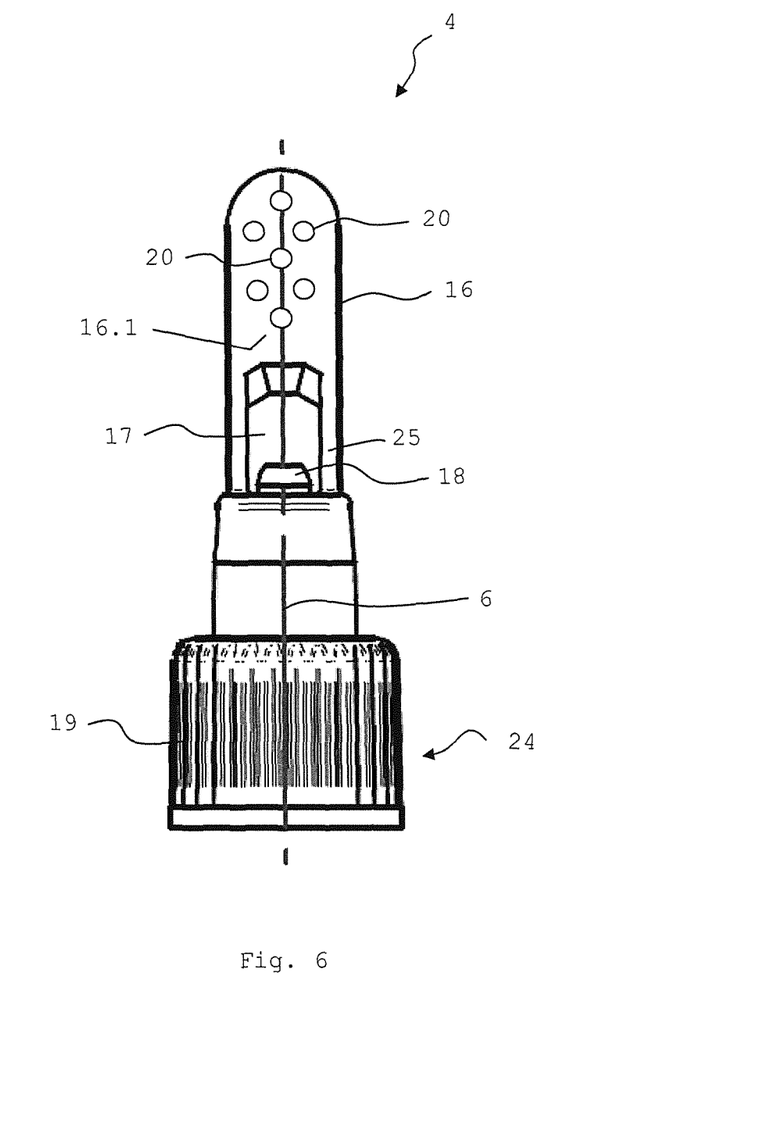
FIG. 6 shows a front view of a further applicator of a tube head of the invention.

The receiving means 16, in particular when formed as a spatula, may be provided with one or more holes 20, the one or more holes 20 preferably having a smaller diameter than the gap 17 (see FIG. 6). By means of the holes 20 the dosing volume of the liquid gathered by the receiving means 16, in particular on the spatula, may be enhanced.

Figure 7:
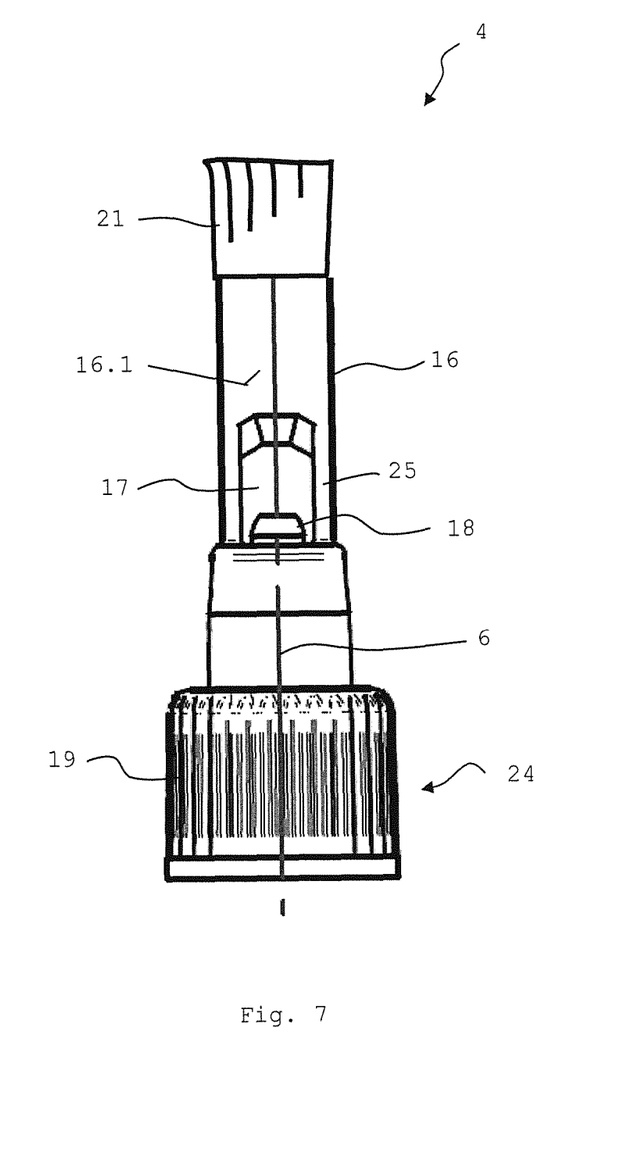
FIG. 7 shows a front view of a still further applicator of a tube head of the invention.

As shown in FIG. 7 the receiving means 16 of the applicator 4 may comprise a brush 21, preferably a brush 21 arranged on/at the flat surface 16.1/the spatula, if distribution of the liquid by a brush is required or advantageous. The brush 21 may be removable, such that it can only be attached when needed.

Figure 8:
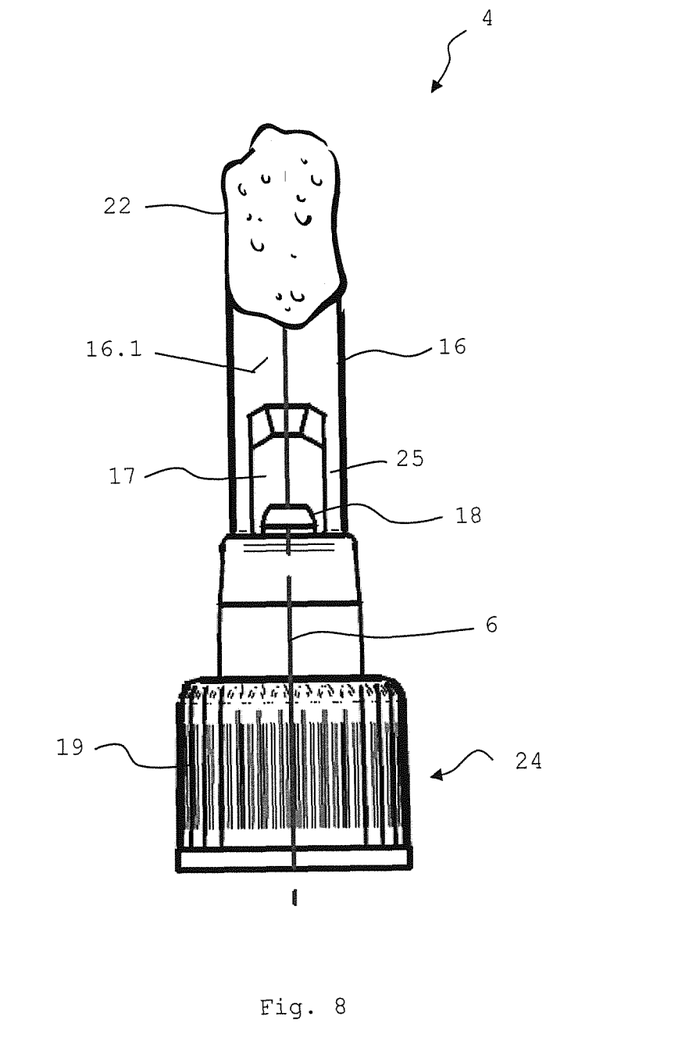
FIG. 8 shows a front view of a still further applicator of a tube head of the invention.

Similarly, the receiving means 16 may comprise a sponge 22, preferably a sponge 22 arranged on/at the flat surface 16.1/the spatula, if distribution of the liquid by a sponge is required or advantageous (see FIG. 8). The sponge 22 may be removable, such that it can only be attached when needed.

Figure 9:
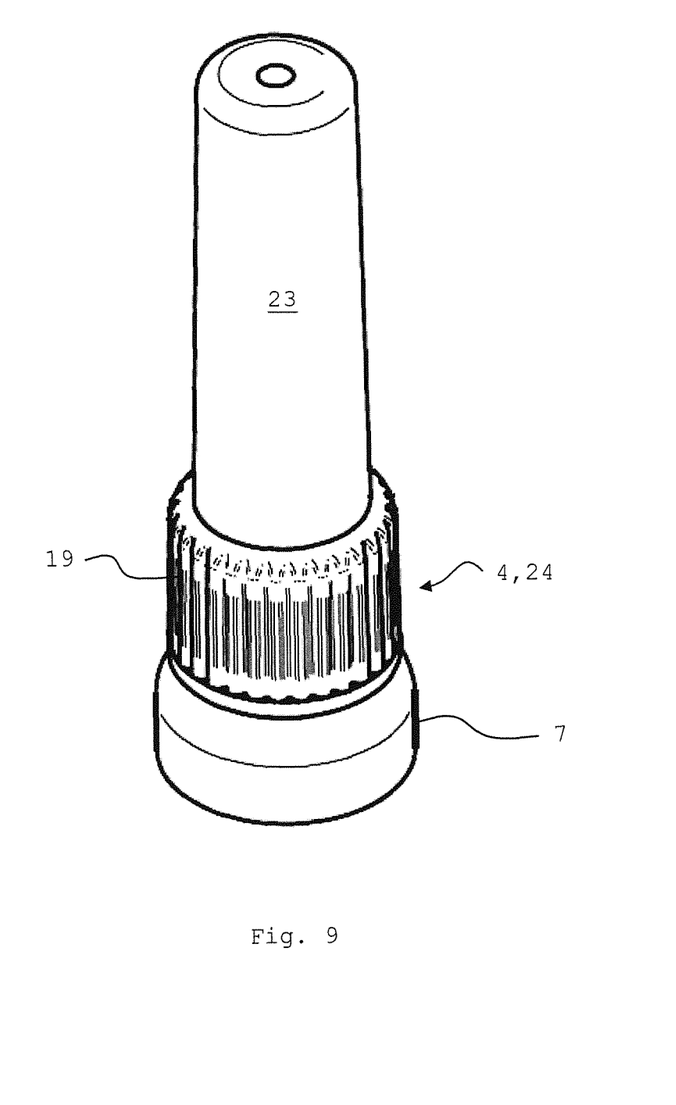
FIG. 9 shows a tube head according to the invention covered by cap.

To protect the applicator 4 and the tube head 1, e.g., from contamination or damage, a removable cap 23 is preferably provided that covers at least those parts of the applicator 4 that may come into contact with the liquid such as the orifice 18 (if provided) and the receiving means 16 (see FIGS. 1 and 9). The cap 23 preferably abuts against the grabbing part 24 of the applicator 4, the grabbing part 24 having a larger outer diameter than the cap 23.

When squeezing the tube body 2 liquid is pressed trough the throttling passage 12 of the insert 10 and its throttling part 11, respectively, and is dispensed as one or more drops from the opening 5 of the spout 3 and, if provided, the orifice 18 of the applicator 4. Each drop is then caught by the receiving means 16 and drawn onto it, wetting it for further application. Several drops can be gathered by the receiving means 16 to obtain the correct dosing volume.

By replacing the applicator 4 with an applicator with different size of the gap 17 different drop sizes can be achieved, or the same drop size can be achieved but for a liquid with different properties, e.g., different viscosity. That is, an applicator 4 with a gap 17 with a gap size may be chosen that is appropriate for the liquid in question.

It is to be understood that while certain embodiments of the present invention have been illustrated and described herein, it is not to be limited to the specific embodiments described and shown.

The invention claimed is:

1. A tube head for provision and application of a liquid, the tube head (1) comprising a spout (3) with an opening (5) for dispensing the liquid in the form of drops, characterized in that an applicator (4) is provided, the applicator (4) being attached to the spout (3) and extending in the longitudinal direction of the spout (3), wherein the applicator (4) comprises receiving means (16) for receiving the liquid dispensed by the spout (3) and wherein a gap (17) is provided between the receiving means (16) and the opening (5) of the spout (3) in the longitudinal direction, wherein receiving means (16) of the applicator (4) comprise a surface (16.1) for receiving the liquid dispensed from the spout (3), the surface (16.1) in particular being flat, wherein the surface (16.1) is provided with one or more holes (20), the one or more holes (20) being smaller in diameter than the gap (17).

2. The tube head according to claim 1, wherein the applicator (4) is detachable from the spout (3).

3. The tube head according to claim 1, wherein the receiving means (16) comprise a sponge (22).

4. The tube head according to claim 1, wherein the receiving means (16) comprise a brush (21).

5. The tube head according to claim 1, wherein the applicator (4) is attached to the spout (3) by locking means (9).

6. The tube head according to claim 1, wherein inside the spout (3) an insert (10) is arranged, the insert (10) having a throttling part (11) whose outer diameter matches the inner diameter of the spout (3), wherein the throttling part (11) has at least one throttling passage (12) through which liquid has to pass to reach the opening (5) of the spout (3).

7. A set of tube heads (1) with at least two tube heads (1) according to claim 1, wherein the size of the gap (17) of the applicator (4) of the tube heads (1) differs for different tube heads (1).

8. A tube with a tube head (1) according to claim 1 and a tube body (2) for containing liquid, the tube head (1) being attached to the tube body (2).

9. The tube according to claim 8, wherein a removable cap (23) is provided.

10. A set of tubes (30) with at least two tubes (30) according to claim 8, wherein the size of the gap (17) of the applicator (4) of the tube head (1) of the tubes (30) differs for different tubes (30).

11. A set of tube heads (1) with at least two tube heads (1), each tube head (1) for provision and application of a liquid, each tube head (1) comprising a spout (3) with an opening (5) for dispensing the liquid in the form of drops, characterized in that an applicator (4) is provided, the applicator (4) being attached to the spout (3) and extending in the longitudinal direction of the spout (3), wherein the applicator (4) comprises receiving means (16) for receiving the liquid dispensed by the spout (3) and wherein a gap (17) is provided between the receiving means (16) and the opening (5) of the spout (3) in the longitudinal direction, wherein the size of the gap (17) of the applicator (4) of the tube heads (1) differs for different tube heads (1).

12. The set of tube heads according to claim 11, wherein the applicator (4) is detachable from the spout (3).

13. The set of tube heads according to claim 11, wherein receiving means (16) of the applicator (4) comprise a surface (16.1) for receiving the liquid dispensed from the spout (3), the surface (16.1) in particular being flat.

14. The set of tube heads according to claim 13, wherein the surface (16.1) is provided with one or more holes (20), the one or more holes (20) being smaller in diameter than the gap (17).

15. The set of tube heads according to claim 11, wherein the receiving means (16) comprise a sponge (22).

16. The set of tube heads according to claim 11, wherein the receiving means (16) comprise a brush (21).

17. The set of tube heads according to claim 11, wherein the applicator (4) is attached to the spout (3) by locking means (9).

18. The set of tube heads according to claim 11, wherein inside the spout (3) an insert (10) is arranged, the insert (10) having a throttling part (11) whose outer diameter matches the inner diameter of the spout (3), wherein the throttling part (11) has at least one throttling passage (12) through which liquid has to pass to reach the opening (5) of the spout (3).

19. A set of tubes (30) with at least two tubes, each with a tube head (1) of the set of tube heads according to claim 11 and a tube body (2) for containing liquid, the tube head (1) being attached to the tube body (2).

20. The set of tubes according to claim 19, wherein a removable cap (23) is provided for each tube.

21. The set of tubes according to claim 19, wherein the size of the gap (17) of the applicator (4) of the tube head (1) of the tubes (30) differs for different tubes (30).

* * * * *